United States Patent
Antonelli Incalzi et al.

(10) Patent No.: US 10,542,942 B2
(45) Date of Patent: Jan. 28, 2020

(54) SYSTEM FOR THE DETECTION AND THE EARLY PREDICTION OF THE APPROACHING OF EXACERBATIONS IN PATIENTS SUFFERING FROM CHRONIC OBSTRUCTIVE BRONCOPNEUMATY

(71) Applicant: LABORATORI DI INFORMATICA APPLICATA DI GIUSEPPE CAPASSO, Cagliari (IT)

(72) Inventors: Raffaele Franco Antonelli Incalzi, Rome (IT); Francesca Maria Barbara Rubiu, Tortoli (IT); Angela Maria Bussu, Tortoli (IT); Giuseppe Capasso, Cagliari (IT); Giulio Iannello, Rome (IT); Mario Merone, Rome (IT); Leonardo Onofri, Terni (IT); Claudio Pedone, Rome (IT); Paolo Soda, Rome (IT)

(73) Assignee: LABORATORI DI INFORMATICA APPLICATA DI GIUSEPPE CAPASSO, Cagliari (IT)

( * ) Notice: Subject to any disclaimer, the term of this patent is extended or adjusted under 35 U.S.C. 154(b) by 0 days.

(21) Appl. No.: 15/577,718

(22) PCT Filed: Jun. 3, 2015

(86) PCT No.: PCT/IT2015/000146
§ 371 (c)(1),
(2) Date: Nov. 28, 2017

(87) PCT Pub. No.: WO2016/194007
PCT Pub. Date: Dec. 8, 2016

(65) Prior Publication Data
US 2018/0153480 A1    Jun. 7, 2018

(51) Int. Cl.
*A61B 5/00* (2006.01)
*G16H 50/30* (2018.01)
(Continued)

(52) U.S. Cl.
CPC .............. *A61B 5/746* (2013.01); *A61B 5/024* (2013.01); *A61B 5/14552* (2013.01);
(Continued)

(58) Field of Classification Search
None
See application file for complete search history.

(56) References Cited

U.S. PATENT DOCUMENTS

2005/0187796 A1    8/2005    Rosenfeld et al.
2007/0276270 A1*   11/2007   Tran .................... A61B 5/0022
                                                        600/508
(Continued)

FOREIGN PATENT DOCUMENTS

WO    2013029617 A1    3/2013

OTHER PUBLICATIONS

Morten H Jensen et al: "Moving prediction of exacerbation in chronic obstructive pulmonary disease for patients in telecare", Journal of Telemedicine and Telecare, Royal Society of Medicine Press, London, GB. vol. 18, Mar. 1, 2012 (Mar. 1, 2012), pp. 99-103, XP009163987, ISNN: 1357-633X, DOI: 10.1258/JTT.2011.110607.
(Continued)

*Primary Examiner* — Thomas S McCormack
(74) *Attorney, Agent, or Firm* — Platinum Intellectual Property LLP (57) ABSTRACT

The present invention concerns a system (S) for the detection and early warning of the incoming of acute events in patients with chronic obstructive pulmonary disease, com-
(Continued)

prising: at least one device (D) for the detection of physiological parameters (R), that can be applied to said patient to be monitored; at least one timer for detecting time intervals, such as date and time, associated with said detected physiological parameters (R); at least one emission device of sound and/or visual alarm signals capable of emitting an sound and/or visual output warning signal, associated with said physiological detected parameters (R); a control logic unit (C), connectable to said at least one device (D) and at least one timer, and capable of controlling said at least one emission signals device, suitable to receive in input said physiological detected parameters (R) and said time intervals, said control logic unit (C) being provided with a processing program, in which thresholds of predetermined values reached by said physiological parameters (R) are initially stored, which runs the following steps: associating said detected physiological parameters (R) with the time intervals, in which the detection has taken place; for every detection time instant, sending said physiological parameters (R) measured at a statistical indices calculation algorithm; comparing said statistical indexes obtained in the preceding step with said predetermined threshold and activating said at least one signals emission device for the emission of a sound and/or visual warning signal if at least one of said statistical indexes exceeds said corresponding predetermined threshold.

9 Claims, 4 Drawing Sheets

(51) Int. Cl.
*A61B 5/024* (2006.01)
*A61B 5/1455* (2006.01)

(52) U.S. Cl.
CPC .......... *A61B 5/7267* (2013.01); *A61B 5/7405* (2013.01); *G16H 50/30* (2018.01)

(56) References Cited

U.S. PATENT DOCUMENTS

2009/0156908 A1* 6/2009 Belalcazar ........... A61B 5/0031
600/301
2014/0221782 A1* 8/2014 Hejlesen ............. G06F 19/3418
600/301

OTHER PUBLICATIONS

Shan Syed Ahmar et al: "Personalized alerts for patients with COPD using pulse oximetry and symptom score", 2014 36th Annual International Conference of the IEEE Engineering in Medicine and Biology Society, IEEE, Aug. 26, 2014, pp. 3164-3167, XP032675090.

* cited by examiner

SYSTEM FOR THE DETECTION AND THE EARLY PREDICTION OF THE APPROACHING OF EXACERBATIONS IN PATIENTS SUFFERING FROM CHRONIC OBSTRUCTIVE BRONCOPNEUMATY

RELATED APPLICATIONS

This application is a United States National Stage Application filed under 35 U.S.C 371 of PCT Patent Application Serial No. PCT/IT2015/000146, filed Jun. 3, 2015, the disclosure of all of which are hereby incorporated by reference in their entirety.

The present invention relates to a system for the detection and the early prediction of the approaching of exacerbations in patients suffering from chronic obstructive broncopneumaty.

Chronic obstructive broncopneumaty or COPD is a chronic pulmonary disease characterized by bronchial obstruction, with partial or not reversible airflow limitation, slowly progressive, caused by chronic inflammation of the airways and of the pulmonary parenchyma.

It is considered the fourth cause of death in the US and the fifth in the world.

Patients with this disease have periodic exacerbations.

Exacerbations phases are more or less long and more or less rapid onset, during which COPD or asthma symptoms get worse, and then the patient, on doctor's advice, should change or intensify the medication that is assuming.

Exacerbations must be reported as soon as possible to the doctor because, especially if not quickly and properly treated, can lead to serious consequences for the asthma or COPD patient, such as hospitalization or even death.

The drugs used to regular daily treat these diseases have as their main purpose to prevent exacerbations.

The invention thus relates to a system of the above kind, studied and realized especially to early detect and report the emergence of said exacerbations or clinically critical situations, called "worrisome events", which could lead to deterioration of health of the COPD subject.

In the following, the description will be directed to system for detection and early warning of exacerbations, but it is clear that the same should not be considered limited to this specific use.

The system in fact can also be employed for the remote multiparametric or monoparametric monitoring in stability conditions.

Currently there are in the literature algorithms that evaluate whether a patient is at COPD exacerbations risk.

An algorithm known in the art takes into account the measurements of a device that detects physiological parameters during a time window, possibly variable, of 30 days duration; then the method determines a regression line a in the plane defined by the Cartesian coordinates of time and $SpO_2$ values.

The coefficient a of the regression line a is compared with a reference value $a_0$.

Assuming $a_0 = -0,0737$, and defining a function $$F(a) = \begin{cases} 1, & se\ a < a_0 \\ 0, & se\ a > a_0 \end{cases}$$

if the value obtained is less than $a_0$, the result obtained is less than 1, indicating that there is an exacerbation phase; instead, if the result obtained is greater than $a_0$, the result obtained will be equal to 0, indicating that the patient is not at exacerbation risk.

The state of the art only considers the risk for a patient affected by COPD to get close to an exacerbation event, without considering other important aspects of the health of the patient as possible dyspnea and tachycardia.

Furthermore, in the prior art a fixed threshold for discriminating whether an event corresponds to an exacerbation is or not is adopted.

For the prediction of the exacerbation is used only $SpO_2$ parameter, while in the literature it has been shown that the predictive capability of exacerbations improves if the trend of both oxygen saturation $SpO_2$ and both heart rate are monitored.

The mathematical expression upon which the known algorithm is based, takes into account only the existing connection between time and oxygen saturation ($SpO_2$), assuming that between these two parameters there is a linear dependence relationship.

Furthermore, the model according to the prior art does not take into account the personal physiological characteristics of the patient, such as the time average of the oxygen saturation ($SpO_2$), which is an information necessary for a correct estimate of the trend of said patient health state.

In the light of the above it is, therefore, object of the present invention to provide a system for the detection and the early prediction of the approaching of exacerbations in patients suffering from chronic obstructive broncopneumaty, taking account the physiological parameters of the patient.

A further object of the present invention is to provide a system, which takes into account time variations of the measurements of physiological parameters of the patient.

It is therefore specific object of the present invention a system for the detection and early warning of the incomingacute events in patients with chronic obstructive pulmonary disease, comprising: at least one device for the detection of physiological parameters, that can be applied to said patient to be monitored; at least one timer for detecting time intervals, such as date and time, associated with said detected physiological parameters; at least one emission device of sound and/or visual alarm signals capable of emitting an sound and/or visual output warning signal, associated with said physiological detected parameters; a control logic unit, connectable to said at least one device and at least one timer, and capable of controlling said at least one emission signals device, suitable to receive in input said physiological detected parameters and said time intervals, said control logic unit being provided with a processing program, in which thresholds of predetermined values reached by said physiological parameters are initially stored, which runs the following steps: associating said detected physiological parameters with the time intervals, in which the detection has taken place; for every detection time instant, sending said physiological parameters measured at a statistical indices calculation algorithm; comparing said statistical indexes obtained in the preceding step with said predetermined threshold and activating said at least one signals emission device for the emission of a sound and/or visual warning signal if at least one of said statistical indexes exceeds said corresponding predetermined threshold.

Further according to the invention, said at least one device is a pulse oximeter that detects the following physiological data: hemoglobin saturation (SpO); and heart rate (HR);

in the following preset time frames, and scanned by said timer: morning hours interval ($C_{morning}$); afternoon hours interval ($C_{Afternoon}$); evening hours interval ($C_{Evening}$).

Still according to the invention, said logic control unit comprises a first unit configured to carry out said association of said detected physiological parameters with the time frames in which the detection has taken place, obtaining the following registrations: morning registrations ($X_{SpO_2}^{morning}$, $X_{HR}^{morning}$); afternoon registrations ($X_{SpO_2}^{afternoon}$, $X_{HR}^{afternoon}$); and evening registrations ($X_{SpO_2}^{evening}$, $X_{HR}^{evening}$); and a second unit, comprising a neural network implemented with a Binary Finite State Machine (BFSM), configured to process said grouped input data, according to said processing program.

Preferably according to the invention, said Binary Finite State Machine (BMSF) runs a first calibration step for setting said predetermined thresholds of values P=($\varepsilon$, Weight $SpO_2$, WeightHR, $\kappa$, $\lambda$), representing the typical trends of said physiological parameters of hemoglobin saturation ($SpO_2$) and heart rate (HR) measurable from said patient to be monitored, and a second learning step of said physiological parameters of hemoglobin saturation ($SpO_2$) and heart rate (HR), wherein said Binary Finite State Machine (BMSF) learns the trend of said hemoglobin saturation ($SpO_2$) and heart rate (HR) of said specific patient to be monitored in said preset time frames of the morning ($C_{Morning}$), in the afternoon ($C_{Afternoon}$) and evening ($C_{Evening}$).

Further according to the invention, said processing program performs the following steps for the calculation of said statistical indices: calculation of the average of said registrations of the morning ($X_{SpO_2}^{morning}$, $X_{HR}^{morning}$), afternoon ($X_{SpO_2}^{afternoon}$, $X_{HR}^{afternoon}$) and evening ($X_{SpO_2}^{evening}$, $X_{HR}^{evening}$), obtaining the values of the average of the morning ($Average_{morning(SpO_2)}$, $Average_{morning(HR)}$), afternoon ($Average_{afternoon(SpO_2)}$, $Average_{afternoon(HR)}$) and evening ($Average_{evening(SpO_2)}$, $Average_{evening(HR)}$); calculating the standard deviation of said registrations of the morning ($X_{SpO_2}^{morning}$, $X_{HR}^{morning}$), afternoon ($X_{SpO_2}^{afternoon}$, $X_{HR}^{afternoon}$) and evening ($X_{SpO_2}^{evening}$, $X_{HR}^{evening}$), obtaining the values of the standard deviation of the morning ($Devst_{morning(SpO_2)}$, $Devst_{morning(HR)}$), afternoon ($Devst_{afternoon(SpO_2)}$, $Devst_{afternoon(HR)}$) and evening ($Devst_{evening(SpO_2)}$, $Devst_{evening(HR)}$); calculating a weighted combination, or Oximetry Weighted Score (WOS) for each class time:

$$WOS(X_{SPO_2}, X_{HR}) = \frac{-Weight_{SPO_2}\left(\frac{X_{SPO_2} - Average(SPO_2)}{Devst(SPO_2)}\right) + Weight_{HR}\left(\frac{X_{HR} - Average(HR)}{Devst(HR)}\right)}{Weight_{SPO_2} + Weight_{HR}}$$

comparing said statistical indexes obtained in previous steps with said predetermined values thresholds.

Still according to the invention, said Binary Finite State Machine (BMSF) evolves in the following states associated to critical warning events: HR Alarm when for two consecutive registrations (R) the condition $X_{HR}>Average_{HR}+K*Devst_{HR}$ occurs, in which the value K is determined in said self-learning step; Oximetryscore Punctual Alarm when the condition $WOS(X_{SpO_2}, X_{HR})>WOS(X_{SpO_2},$ Average (HR)) occurs; $SpO_2$ Alarm when $X_{SpO_2} \leq \gamma$, con $\gamma \in [80,95]$, Missing Data Alarm in the case of two missing consecutive registrations (R), Alarm Oximetry score associated with an alarm place reached when recording fulfils one of the following conditions:

Warning1: $WOS(X_{SpO_2}, X_{HR})>WOS(SPO_{2critical}+\varepsilon,$ Average(HR))$*B_1^\lambda$ Warning2: $WOS(X_{SpO_2}, X_{HR})>WOS(SPO_{2critical}+\varepsilon,$ Average(HR))$*B_2^\lambda$ Warning3: $WOS(X_{SpO_2}, X_{HR})>WOS(SPO_{2critical}+\varepsilon,$ Average(HR))$*B_3^\lambda$ AllarmWarrisomeOximetryScore:WOS
$(X_{SpO_2}, X_{HR})>WOS(SPO_{2critical}+\varepsilon,$Average (HR))$*B_3^\lambda$ wherein B1, B2, B3 $\varepsilon$[0, 1] and $SpO_{2\ critical}$ is the critical value of oxygen saturation, normally equal to 0.9%.

Preferably according to the invention, said HR Alarm, Oximetryscore Punctual Alarm, $SpO_2$ Alarm, Missing Data Alarm and Alarm Oximetry score states are provided as input to said emission device of sound and/or visual alarm signals, which emits sound and/or visual signals for each corresponding state.

Further according to the invention, said system could comprise a plurality of sensors capable of detecting further physiological parameters from said monitored patient.

Still according to the invention, said sensors comprise an accelerometer for detecting movements of said patient and/or a spirometer for the detection of pulmonary volume of said patient to provide input to said control logic unit.

Preferably according to the invention, in said calibration step of said Finite State Machine (BMSF), a self-learning algorithm is used, which configuration parameters P=($\varepsilon$, Weight $SpO_2$, WeightHR, $\kappa$, $\lambda$) can be set by a user.

Further according to the invention, said Finite State Machine (MSFB) learns said parameters P according to the following steps: providing a validation set of registrations (R) on which, fixed a possible configuration of the parameters $\hat{P}$, the algorithm is tested and the weighted accuracy $acc_{weighted}$ is estimated; testing said parameters, by setting the data value WeightHR equal to 1, while the value of the datum Weight $SpO_2$ can vary between 1 and 20; determining the set of said parameters $\hat{P}$ by performing the Cartesian product of the possible combinations of parameters P=($\varepsilon$, Weight $SpO_2$, WeightHR, $\kappa$, $\lambda$); selecting the parameter configuration P* to be used by said system (S), by selecting a combination of said parameters that maximizes the weighted accuracy value according to the formula P*=arg max$_t$ ($acc_{weighted}(\hat{P}_t)$).

Still according to the invention, said parameter $\lambda \in [0.1, \ldots, i, \ldots, 0.09] \cup [1, \ldots, j, \ldots, 10]$, with i $\in \Re$ and j$\in \Re$ and such that $\lambda_{+1}-\lambda_1=0.01$ and said parameter $\kappa \in [1, \ldots, i \ldots, 10]$ with i $\in \aleph$.

The present invention will be now described, for illustrative but not limitative purposes, according to its preferred embodiments, with particular reference to the figures of the enclosed drawings, wherein.

Figure 1:
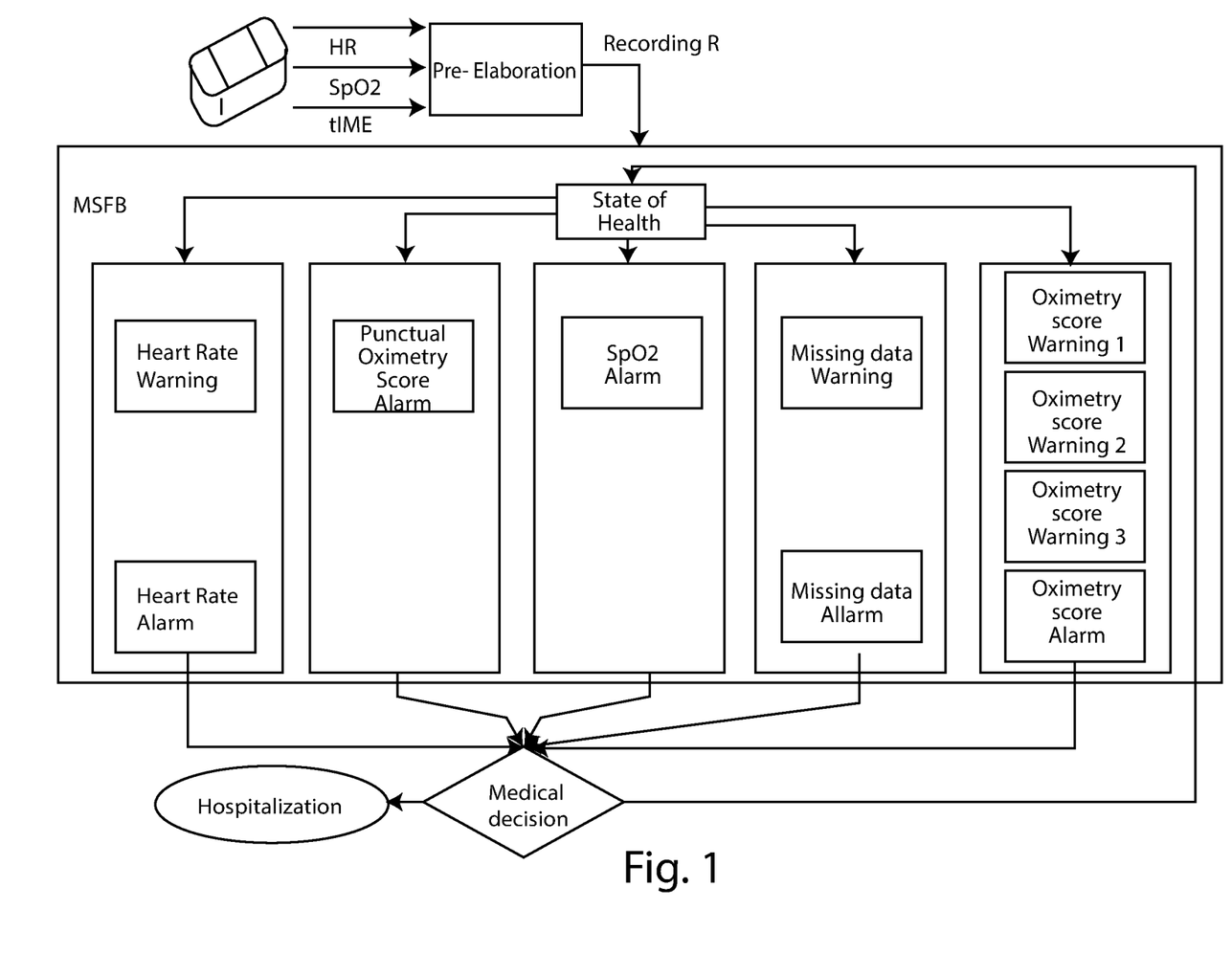
FIG. 1 shows a block diagram of the system for the detection and early warning of the incoming acute events in patients with chronic obstructive pulmonary disease.

Referring to the enclosed figures, it is seen that the system S for the detection and prediction of acute events in patients suffering from chronic obstructive broncopneumaty, object of the present invention, comprises a device D for the acquisition of physiological data of a patient suffering from chronic obstructive broncopneumaty, such as a pulse oximeter.

The data detected by said device D are mainly the saturation of hemoglobin, also called $SpO_2$, and the heart rate, also called Heart Rate or HR, for said patient.

Said system S includes a timer for the detection of temporal data, such as date and time are associated with said physiological data, as it will be described in detail hereinafter.

Said system S may comprise a plurality of sensors, not shown in the figure, capable of detecting further physiological parameters from said patient, such as an accelerometer for detecting movements of said patient and a spirometer for the detection of pulmonary volume of said patient.

Said system S also comprises a control logic unit C which receives in input said physiological data and said time data, hereinafter referred to as input data, acquired from said device D, from said plurality of sensors and from said timer, processes said data input in accordance with a predetermined program, which will be described in detail hereinafter, and supplies processed data at the output, hereinafter referred to as output data.

Said control logic unit C comprises a first part C, which carries out a pre-processing of said input data, and a second part C, comprising a recognition algorithm of acute events, implemented by means of a Binary Finite State Machine, or even BMSF, that performs the processing of said pre-processed input data, as will it be described in detail hereinafter.

Said system S also comprises a device for the emission of sound and/or visual warning alarm, not shown, which receives in input said output data from said control logic unit C, and outputs warning signals, corresponding to said output data according to a predetermined logic, which will be described in detail hereinafter.

Said data input to said control logic unit C are in particular four, the value of the hemoglobin saturation percentage, the value of the heart rate HR measured by said pulse oximeter and the date and time at which the measurement or registration R takes place, provided by said timer.

Such input data are formally designated by the triad $(X_{SPO2}, X_{HR}XHR, t)$, where the value t indicates both the date and time of the registrations R.

Registrations R can be made at different times of day, according to which said input data are classified.

In particular, three possible hourly classes are defined:
morning class, indicated by $C_{morning}$, containing all the registrations R in the morning if the registration time belongs to the time slot of the morning, said registrations are indicated by $(X_{SpO_2}^{morning}, X_{HR}^{morning})$;
afternoon class, indicated by $C_{afternoon}$ containing all the registrations R in the afternoon if the registration time belongs to the time slot of the afternoon, said registrations are indicated by $(X_{SpO_2}^{afternoon}, X_{HR}^{afternoon})$;
evening class, indicated by $C_{evening}$, containing all the registrations R in the evening if the registration time belongs to the time slot of the evening, said registrations are indicated by $(X_{SpO_2}^{evening}, X_{HR}^{evening})$.

Said time slots of each class are set and adapted to the specific needs of the patient and may be variable both in number and in duration.

Said first part C carries out the association between each registration R and the hourly class to which they belong.

Said data output from said control logic unit C consist in a mean and standard deviation of a time window of defined amplitude, for example 10 days, of each of said input data, which are indicated with the following symbols:

$(Average_{morning(SpO_2)}, Devst_{morning(SpO_2)}, (Average_{morning(HR)}, Devst_{morning(HR)})$;
$(Average_{afternoon(SpO_2)}, Devst_{afternoon(SpO_2)}), (Average_{afternoon(HR)}, Devst_{afternoon(HR)})$;
$(Average_{evening(SpO_2)}, Devst_{evening(SpO_2)}), (Average_{evening(HR)}, Devst_{evening(HR)})$.

Said output data from said control logic unit C are associated to said sound and/or visual warning signals, as it will be described in detail hereinafter.

Said sound and/or visual warning signal emitted by said emission device can be listed as follows:
HR alarm associated with a HR registration over a predetermined threshold, to which corresponds a possible sinus tachycardia;
score punctual Oximetry Alarm associated with a sharp variation of the recordings of $SpO_2$ and HR over predetermined values, which corresponds to a possible dyspnea;
$SpO_2$ Alarm related to a $SpO_2$ registration lower than a predetermined threshold, to which a possible hypoxemia corresponds;
Alarm missing data associated with two consecutive missing recordings with respect to the established protocol by the treating doctor of said patient, due to malfunction of said pulse oximeter D, or due to a general ill state of the patient, who is not able to perform the registration;
Alarm Oximetry score associated with a negative trend of $SpO_2$ and HR recordings, which corresponds to the incoming of possible exacerbations of the disease.

According to the specific warning signal, said emission device signals may generate an alarm sound or a visual signal.

The operation of the system S described above is as follows.

When a patient suffering from chronic obstructive broncopneumaty decides to use the system S described above, he agrees with his own treating doctor a protocol by which he determines the number of registrations R to be made and the time intervals in which carrying out said registrations R.

In said system S it is possible both setting initial parameters and performing a standard calibration step, so as to make said system S adapted for the physiological parameters of said monitored patient, so that it fits to the decisions process of the specialist of the pathology.

Therefore, in an initial calibration step of about 10 days duration, duration that is indicative and illustrative, which can be customized to the specific characteristics of each patient, said pulse oximeter D acquires repeatedly during the day physiological data of said patient monitored, in particular the typical values of $SpO_2$ and HR of said monitored patient, in different time instants within the time frame of a day.

Said first part $C_1$ of said control logic unit C associates said physiological parameters to the initial time instants, in which registration was effected, so as to configure a typical trend of said physiological parameters in the time period of one day.

These initial physiological parameters, associated with time intervals, are then sent from said first part $C_1$ to said second part $C_2$ which, being a supervised learning algorithm, has the ability to learn and adapt to the physiological characteristics of said monitored patient, customizing then the specific physiological parameters of the patient at different times of the day.

For this purpose the algorithm requires that the measurements acquired in the aforesaid initial calibration stage are labeled, for example by a specialist, so that the learning algorithm can adapt to the correct decision-making process. The learning consists in optimizing threshold parameters with respect to the above said physiological characteristics.

Then following said initial training period, said system S will continue to be modeled on the patient either through self-learning using the input data, either through a possible intervention by the specialist doctor by modifying the configuration parameters for a better response from said system S.

As it will be described in detail hereinafter, said system S is therefore able to detect possible exacerbations, analyzing the correlated trend of $SpO_2$ and HR parameters, through a series of state transitions of said system S that reflect the worsening of the patient monitored until the reaching a place of alarm that shows an initial deterioration of the physiological parameters of the monitored patient, allowing to identify the exacerbations in the early phase.

In particular, said BMSF comprised in said second part $C_2$ of said control logic unit C analyzes the measured values of $SpO_2$ and HR, to create a model of the time evolution of the state of health of said monitored patient.

Figure 2:
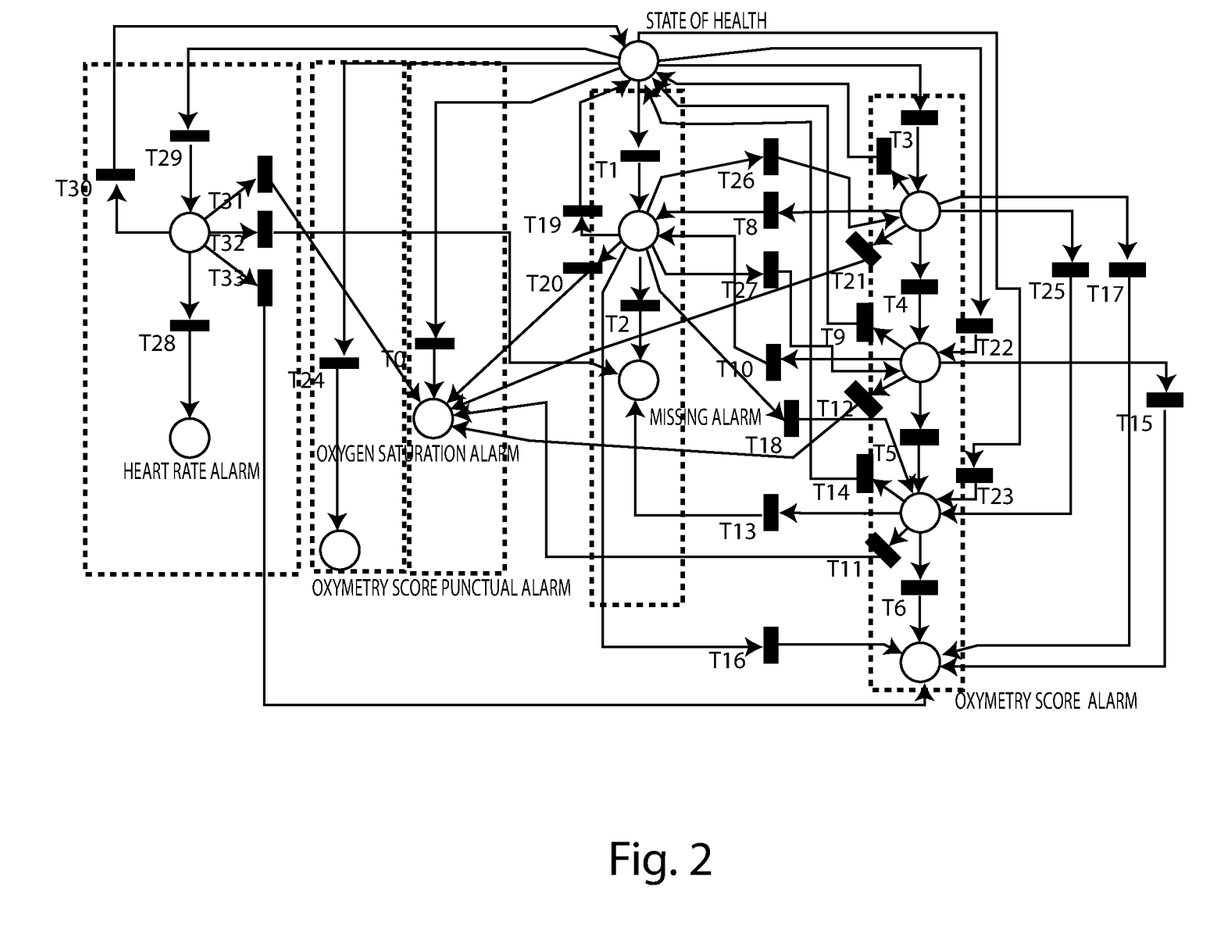
FIG. 2 shows the operation of a part of the system according to the invention.

A BMSF is a particular Petri net, which is a bipartite graph, which defines the following items:

token, shown in FIG. 2 with a black dot, corresponding to the state of said monitored patient, at the moment when said registration R takes place;

places, shown in FIG. 2 with white circles, corresponding to the possible health states of said monitored patient, that are defined by the normal state, in which measured physiological parameters of said monitored patient fall within normal ranges, alert state, in which the physiological parameters measured by said monitored patient presenting a negative trend and alarm state in which measured physiological parameters of said monitored patient correspond to a critical state, for it is necessary a hospitalization of said monitored patient in an hospital, that are also called Worrisome events;

transitions, shown in FIG. 2 with black rectangles, corresponding to clinical evolutions from one place to another.

The places and transitions are called nodes and nodes are interconnected by oriented arcs.

It is only possible connections between nodes of different types.

The dynamic evolution of said system S is represented through the passage of a single token, from one place to the next one, when the transition connecting the two places is enabled, i.e., when the condition linked to that transition is verified.

As described above, those registrations R are pre-processed by said first part $C_1$ of said control logic unit C and then are catalogued according to the time in which they occurred, in three categories of registration, morning, afternoon and evening.

Subsequently, averages and standard deviations of the three registrations categories are calculated, for each hourly class said system S calculates averages and standard deviations both for oxygen saturation measurements and for heart rate ones.

This means that the system S calculates independently the averages and standard deviations of all recordings acquired between times, which may possibly coincide with zero, and the second, which took place during the three hourly classes, or in the morning, afternoon and evening.

Therefore, said system S calculates the above twelve parameters:

(Average$_{morning\ (SpO_2)}$, Devst$_{morning\ (SpO_2)}$), (Average$_{morning(HR)}$, Devst$_{morning(HR)}$);

(Average$_{afternoon(SpO_2)}$, Devst$_{afternoon(SpO_2)}$), (Average$_{afternoon(HR)}$, Devst$_{afternoon(HR)}$);

(Average$_{evening(SpO_2)}$, Devst$_{evening(SpO_2)}$), (Average$_{evening(HR)}$, Devst$_{evening(HR)}$).

Said system S, with each new registration updates the average and standard deviation of the two measurements of the hourly class related to the new registration.

For each pair of measurements made in the same time slot at time $t > t_2$, indicated as ($X_{SPO2}$, $X_{HR}$), it calculates a weighted combination that is called Weighted Oximetry Score (WOS):

$$WOS(X_{SPO_2}, X_{HR}) = \frac{-Weight_{SPO_2}\left(\frac{X_{SPO_2} - Average(SPO_2)}{Devst(SPO_2)}\right) + Weight_{HR}\left(\frac{X_{HR} - Average(HR)}{Devst(HR)}\right)}{Weight_{SPO_2} + Weight_{HR}}$$

where $SpO_2$ and HR represent the sample registrations set used for training said system S.

After the pre-processing step by said first part $C_1$, the data are sent to said second part $C_2$, in particular to said BMSF of said control logic unit C proceeds starting from the place obtained from the previous event.

Figure 3:
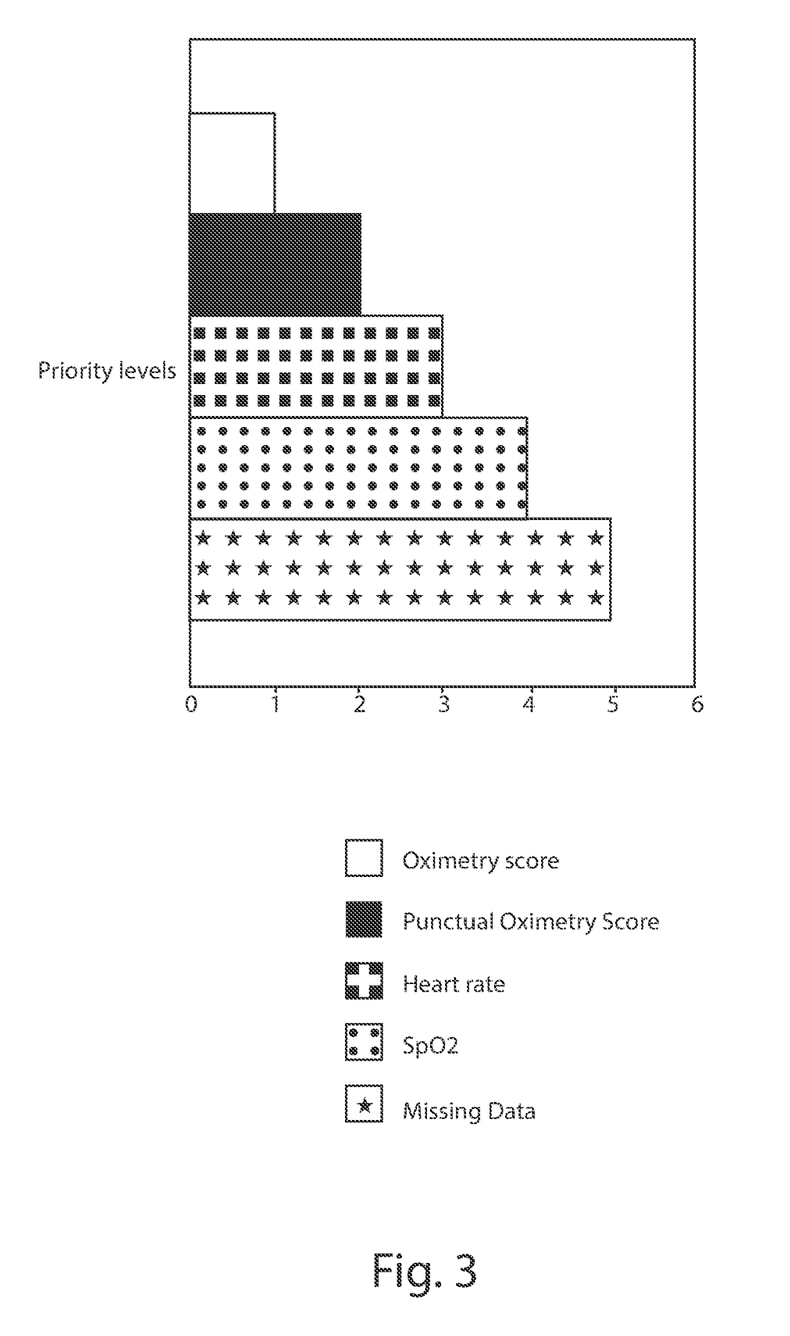
FIG. 3 shows a graph relating to the priority levels associated with critical events detected by the system according to the invention.
Figure 4:
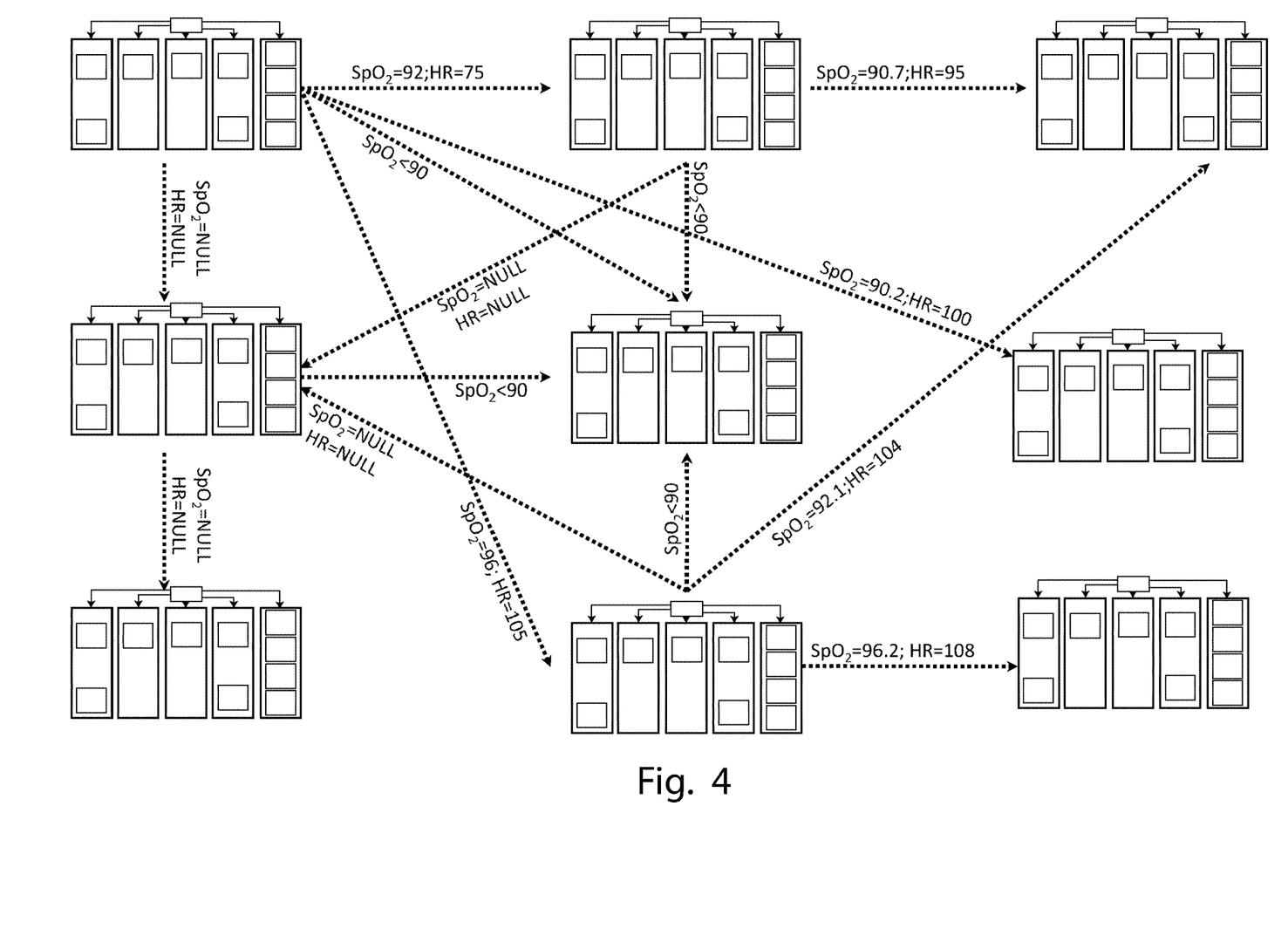
FIG. 4 shows a possible management of the priority levels of critical events; and In the various figures, similar parts will be indicated by the same reference numbers.

Referring to FIG. 3, and in particular to the five vertical chains of events represented therein, the main network ways, from left to right, correspond to the above-described audio and/or visual warning signals emitted by said emission device, which occur in the following situations:

HR Alarm is associated to a single place of alarm and is reached when it occurs, for two consecutive events, the condition: $X_{HR}$)Average$_{HR}$+K*Devst$_{HR}$, in which the value K is determined in the self-learning step of said BMSF.

punctual Oximetryscore Alarm is associated with one place of alarm reached when the condition WOS($X_{SpO_2}$, ($X_{SpO_2}$, $X_{HR}$)>WOS($X_{SpO_2}$, Average(HR)) occurs.

$SpO_2$ Alarm is associated with a unique place of alarm that is achieved when $X_{SpO_2} \leq \gamma$, where $\gamma \in [80,95]$;

Alarm missing data is associated with a unique alarm place that is reached at the first missing registration and from one missing alarm place that is reached in case of two consecutive missing measurements;

Alarm Oximetry score associated with a alarm place reached when the registration verify one of the following conditions:

Warning1: WOS($X_{SPO_2}$,$X_{HR}$)>WOS(SPO$_{2critical}$+$\varepsilon$, Average(HR))*$B_1^\lambda$ Warning2: WOS($X_{SPO_2}$,$X_{HR}$)>WOS(SPO$_{2critical}$+$\varepsilon$, Average(HR))*$B_2^\lambda$ Warning3: WOS($X_{SPO_2}$,$X_{HR}$)>WOS(SPO$_{2critical}$+$\varepsilon$, Average(HR))*$B_3^\lambda$ AllarmWarrisomeOximetryScore: WOS($X_{SPO_2}$,$X_{HR}$)>WOS(SPO$_{2critical}$, Average(HR))

where the parameters B1, B2, B3 vary between 0 and 1, for example can be set equal to 0.25, 0.50, 0.75, also SpO$_{2\ critical}$ is the critical value of oxygen saturation, normally equal to 0.9, Average(HR) is the arithmetic average of the registrations of the heart rate based on the time slot to which the registrations belongs during the observation time, while k, λ and ε are parameters that can be set during configuration of the system S.

The dynamic evolution of the token can develop both on the main vertical paths, as shown in FIG. 1, and in possible alternative paths, which connect them with each other, as shown in FIG. 2.

Transitions that precede a place all have the same condition.

Competitive situations or situations in which different conditions occur simultaneously belonging to several major chains are solved based on the priority levels of the chains represented in FIG. 3.

A part of the chain corresponding to missing measurements, the same input is capable of activating simultaneously more than one transition.

In particular, starting from a place corresponding to the state of health of said monitored patient, if the registration R made at a determined hourly class shows a sudden decay of $SpO_2$ below a predetermined alarm threshold, associated with a small increase of HR, transitions corresponding to timely Oximetryscore Alarm, $SpO_2$ Alarm and Alarm Oximetry score chains would be activated simultaneously.

However, due to the different priority levels shown in FIG. 3, only one transition corresponding to the chain alarm is activated, allowing the passage of the token from one place to the next in a uniform way.

The table below shows all the possible transitions and the conditions for its activation:

| Transitions | Activation condition |
| --- | --- |
| $T_1, T_2, T_{32}, T_{13}, T_8, T_{10}$ | Missing measiring event |
| $T_0, T_{20}, T_{21}, T_{31}, T_{11}, T_{12}$ | Measure $X_{SPO_2} < 90$ |
| $T_{28}, T_{29}$ | $X_{HR} > \text{Average}_{(HR)} + K * \text{Dev}_{st(SPO_2)}$ |
| $T_3, T_{26}$ | $WOS(X_{SPO_2}, X_{HR}) > WOS(SPO_{2critical} + \varepsilon, \text{Average(HR)}) * 0.25^\lambda$ |
| $T_4, T_{22}, T_{27}$ | $WOS(X_{SPO_2}, X_{HR}) > WOS(SPO_{2critical} + \varepsilon, \text{Average(HR)}) * 0.50^\lambda$ |
| $T_5, T_{18}, T_{23}, T_{25}$ | $WOS(X_{SPO_2}, X_{HR}) > WOS(SPO_{2critical} + \varepsilon, \text{Average(HR)}) * 0.75^\lambda$ |
| $T_6, T_{15}, T_{16}, T_{17}, T_{33}$ | $WOS(X_{SPO_2}, X_{HR}) > WOS(SPO_{2critical} + \varepsilon, \text{Average(HR)})$ |
| $T_{13}, T_{14}, T_9, T_7, T_{30}$ | $WOS(X_{SPO_2}, X_{HR}) \leq WOS(SPO_{2critical} + \varepsilon, \text{Average(HR)}) * 0.25^\lambda$ |

As regards the self-learning of said BMSF, using a self-learning algorithm, whose configuration parameters P (ε, Weight $SpO_2$, WeightHR, κ, λ) are learned on the basis of the labeling of alarm events by the doctor during said initial training step of said monitored patient.

The learning procedure of the aforesaid parameters takes place according to the following steps:
at first, providing a set of validation of registrations R is necessary, on which, once fixed a possible configuration of the parameters $\hat{P}$, the algorithm is tested and the weighted accuracy, called $acc_{Weighted}$ is estimated.

The table below shows a matrix of weights for the calculation of $acc_{Weighted}$.

|  | Health state | Missing data alarm | Oximetry score alarm | HR alarm, Oximetry punctual alarm score, $SpO_2$ alarm |
| --- | --- | --- | --- | --- |
| Health state | 1 | 1 | 1 | 1 |
| Missing data alarm | 1 | 1 | 2 | 1 |
| Oximetry score alarm | 2 | 1 | 1 | 1 |
| HR alarm, Oximetry punctual alarm score, $SpO_2$ alarm | 1 | 1 | 1 | 1 |

Then parameters $\hat{P}$ are tested.

Referring to the equation of the calculation of the value $WOS(X_{SpO_2}, X_{HR})$, considering the configuration parameters $\text{Weight}(X_{SpO_2})$, $\text{Weight}(X_{HR})$ due to the relative nature of the two weights, fixing one of the two parameters and varying the other is sufficient.

It has been chosen to fix the parameter $\text{Weight}(X_{HR})$ equal to 1, while $\text{Weight}(X_{SpO_2})$ varies between 1 and 20.

The parameter $\lambda \in [0.1, \ldots, i, \ldots, 0.09] \cup [1, \ldots, j, \ldots, 10]$, with $i \in \mathfrak{R}$ and $j \in \mathfrak{R}$ and such that $\lambda_{i+1} - \lambda_i = 0.01$.

The parameter $\kappa \in [1, \ldots, i, \ldots 10]$, with $i \in \aleph$.

The set of parameters $\hat{P}$ is given by the Cartesian product between the possible combinations of parameters P (ε, Weight $SpO_2$, WeightHR, κ, λ).

The configuration of the parameters used in said system S, indicated by $P^*$ is equal to the combination that maximizes the value of the accuracy weighing, or $P^* = \arg\max_t (ac\text{-}c_{weighted}(\hat{P}_t))$.

According to what is described, said system S has predictive capabilities since the states of alert, prior to the alarm can be regarded as different levels of probability that the patient may have an exacerbation, sending alert signals even when the patient does not show symptoms and the exacerbation is still in latent stage. Said system S allows identifying the approaching of a dangerous event for said monitored patient, associated with the degeneration of the negative state of health of the patient, as well as non-acquisition of the measurements themselves.

Also, the use of the BMSF allows monitoring the health conditions evolving over time.

The present invention has been described for illustrative but not limitative purposes, according to its preferred embodiments, but it is to be understood that modifications and/or changes can be introduced by those skilled in the art without departing from the relevant scope as defined in the enclosed claims.

The invention claimed is:

1. A system (S) for the detection and early warning of the incoming acute events in patients with chronic obstructive pulmonary disease, comprising:
    at least one device (D) for the detection of physiological parameters (R), that can be applied to said patient to be monitored;
    at least one timer for detecting time intervals, such as date and time, associated with said detected physiological parameters (R);
    at least one emission device of sound and/or visual alarm signals capable of emitting an sound and/or visual output warning signal, associated with said physiological detected parameters (R);
    a control logic unit (C), connectable to said at least one device (D) and at least one timer, and capable of controlling said at least one emission signals device, suitable to receive in input said physiological detected parameters (R) and said time intervals, said control logic unit (C) being provided with a processing program, in which thresholds of predetermined values reached by said physiological parameters (R) are initially stored, which runs the following steps:
associating said detected physiological parameters (R) with the time intervals, in which the detection has taken place;
for every detection time instant, sending said physiological parameters (R) measured at a statistical indices calculation algorithm;
comparing said statistical indexes obtained in the preceding step with said predetermined threshold and activating said at least one signals emission device for the emission of a sound and/or visual warning signal if at least one of said statistical indexes exceeds said corresponding predetermined threshold;
wherein said at least one device (D) is a pulse oximeter that detects the following physiological data:
hemoglobin saturation (SpO);
heart rate (HR);
in the following preset time frames, and scanned by said timer:
morning hours interval ($C_{Morning}$);
afternoon hours interval ($C_{Afternoon}$);
evening hours interval ($C_{Evening}$),
wherein said logic control unit (C) comprises
a first unit (C) configured to carry out said association of said detected physiological parameters (R) with the time frames in which the detection has taken place, obtaining the following registrations:
morning registrations ($X_{SpO_2}^{morning}$, $X_{HR}^{morning}$);
afternoon registrations ($X_{SpO_2}^{afternoon}$, $X_{HR}^{afternoon}$);
evening registrations ($X_{SpO_2}^{evening}$, $X_{HR}^{evening}$); and
a second unit ($C_2$), comprising a neural network implemented with a Binary Finite State Machine (BFSM), configured to process said grouped input data, according to said processing program, and
wherein said Binary Finite State Machine (BMSF) runs
a first calibration step for setting said predetermined thresholds of values P=($\varepsilon$, Weight SpO$_2$, WeightHR, $\kappa$, $\lambda$), representing the typical trends of said physiological parameters of hemoglobin saturation (SpO$_2$) and heart rate (HR) measurable from said patient to be monitored, and
a second learning step of said physiological parameters of hemoglobin saturation (SpO$_2$) and heart rate (HR), wherein said Binary Finite State Machine (BMSF) learns the trend of said hemoglobin saturation (SpO$_2$) and heart rate (HR) of said specific patient to be monitored in said preset time frames of the morning ($C_{Morning}$), in the afternoon ($C_{Afternoon}$) and evening ($C_{Evening}$).

2. The system(s) according to claim 1, characterized in that said processing program performs the following steps for the calculation of said statistical indices:
calculation of the average of said registrations of the morning ($X_{SpO_2}^{morning}$, $X_{HR}^{morning}$), afternoon ($X_{SpO_2}^{afternoon}$, $X_{HR}^{afternoon}$) and evening ($X_{SpO_2}^{evening}$, $X_{HR}^{evening}$), obtaining the values of the average of the morning (Average$_{morning(SpO_2)}$, Average$_{morning(HR)}$), afternoon (Average$_{afternoon(SpO_2)}$, Average$_{afternoon(HR)}$) and evening (Average$_{evening(SpO_2)}$, Average$_{evening(HR)}$);
calculating the standard deviation of said registrations of the morning ($X_{SpO_2}^{morning}$, $X_{HR}^{morning}$), afternoon ($X_{SpO_2}^{afternoon}$, $X_{HR}^{afternoon}$) and evening ($X_{SpO_2}^{evening}$, $X_{HR}^{evening}$), obtaining the values of the standard deviation of the morning (Devst$_{morning(SpO_2)}$, Devst$_{morning(HR)}$), afternoon (Devst$_{afternoon(SpO_2)}$, Devst$_{afternoon(HR)}$) and evening (Devst$_{evening(SpO_2)}$, Devst$_{evening(HR)}$);
calculating a weighted combination, or Oximetry Weighted Score (WOS) for each class time:

$$WOS(X_{SPO_2}, X_{HR}) = \frac{-Weight_{SPO_2}\left(\frac{X_{SPO_2} - Average(SPO_2)}{Devst(SPO_2)}\right) + Weight_{HR}\left(\frac{X_{HR} - Average(HR)}{Devst(HR)}\right)}{Weight_{SPO_2} + Weight_{HR}}$$

comparing said statistical indexes obtained in previous steps with said predetermined values thresholds.

3. The system(s) according to claim 2, characterized in that said Binary Finite State Machine (BMSF) evolves in the following states associated to critical warning events:
HR Alarm when for two consecutive registrations (R) the condition $X_{HR}$>Average$_{HR}$+K*Devst$_{HR}$ occurs, in which the value K is determined in said self-learning step;
Oximetryscore Punctual Alarm when the condition WOS ($X_{SpO_2}$, $X_{HR}$)>WOS($X_{SpO_2}$Average(HR)) occurs;
SpO$_2$ Alarm when $X_{SpO_2} \leq \gamma$, wherein $\gamma \in [80,95]$
Missing Data Alarm in the case of two missing consecutive registrations (R);
Alarm Oximetry score associated with an alarm place reached when recording fulfils one of the following conditions:

Warning1: WOS($X_{SpO_2}$,$X_{HR}$)>WOS(SPO$_{2critical}$+$\varepsilon$, Average(HR))*$B_1^\lambda$ Warning2: WOS($X_{SpO_2}$,$X_{HR}$)>WOS(SPO$_{2critical}$+$\varepsilon$, Average(HR))*$B_2^\lambda$ Warning3: WOS($X_{SpO_2}$,$X_{HR}$)>WOS(SPO$_{2critical}$+$\varepsilon$, Average(HR))*$B_3^{80}$ AllarmWarrisomeOximetryScore: WOS ($X_{SPO_2}$,$X_{HR}$)>WOS(SPO$_{2critical}$+$\varepsilon$,Average(HR))

wherein B1, B2, B3 $\varepsilon$[0, 1] and SpO$_2$ $_{critical}$ is the critical value of oxygen saturation, normally equal to 0.9%.

4. The system(s) according to claim 3, characterized in that said HR Alarm, Oximetryscore Punctual Alarm, SpO$_2$ Alarm, Missing Data Alarm and Alarm Oximetry score states are provided as input to said emission device of sound and/or visual alarm signals, which emits sound and/or visual signals for each corresponding state.

5. The system(s) according to claim 1, characterized in that it comprises a plurality of sensors capable of detecting further physiological parameters from said monitored patient.

6. The system(s) according to claim 5, characterized in that said sensors comprise an accelerometer for detecting movements of said patient and/or a spirometer for the detection of pulmonary volume of said patient to provide input to said control logic unit (C).

7. The system(s) according to claim 1, characterized in that in said calibration step of said Finite State Machine (BMSF), a self-learning algorithm is used, which configuration parameters P=($\varepsilon$, Weight SpO$_2$, WeightHR, $\kappa$, $\lambda$) can be set by a user.

8. The system(s) according to claim 1, characterized in that said Finite State Machine (MSFB) learns said parameters P according to the following steps:

providing a validation set of registrations (R) on which, fixed a possible configuration of the parameters $\hat{P}$, the algorithm is tested and the weighted accuracy $acc_{weighted}$ is estimated;

testing said parameters, by setting the data value WeightHR equal to 1, while the value of the datum Weight $SpO_2$ can vary between 1 and 20;

determining the set of said parameters $\hat{P}$ by performing the Cartesian product of the possible combinations of parameters $P=(\varepsilon, \text{Weight SpO}_2, \text{WeightHR}, \kappa, \lambda)$;

selecting the parameter configuration P* to be used by said system (S), by selecting a combination of said parameters that maximizes the weighted accuracy value according to the formula $P^* = \arg\max_t (acc_{weighted}(\hat{P}_t))$.

9. The system(s) according to claim 3, characterized in that said parameter $\lambda \in [0.1, \ldots, i, \ldots, 0.09] \cup [1, \ldots, j, \ldots, j \ldots, 10]$, with $i \in \Re$ and $j \in \Re$ and such that $\lambda_{i+1} - \lambda_i = 0.01$ and said parameter $k \in [1, \ldots, i, \ldots, 10]$ with $i \in \aleph$.

* * * * *